US00PP15133P3

(12) United States Plant Patent
Redman

(10) Patent No.: US PP15,133 P2
(45) Date of Patent: Sep. 7, 2004

(54) CHRYSANTHEMUM PLANT NAMED 'SAFARI TIME GOLDEN'

(50) Latin Name: *Chrysanthemum morifolium*
Varietal Denomination: Safari Time Golden

(75) Inventor: Ruth Redman, Bognor Regis (GB)

(73) Assignee: Cleangro LTD (GB)

( * ) Notice: Subject to any disclaimer, the term of this patent is extended or adjusted under 35 U.S.C. 154(b) by 0 days.

(21) Appl. No.: 10/365,164

(22) Filed: Feb. 11, 2003

(65) Prior Publication Data

US 2004/0158909 P1 Aug. 12, 2004

(51) Int. Cl.[7] ..... A01H 5/00
(52) U.S. Cl. ..... Plt./295
(58) Field of Search ..... Plt./295, 286

(56) References Cited

U.S. PATENT DOCUMENTS

PP11,447 P 7/2000 Boeder ..... Plt./295

OTHER PUBLICATIONS

Brummitt, Dick, Chrysanthemum once again, 1997, The Garden, pp. 662–663.*
1998 Ficor catalog, listing the varieties 'Velvet Time' and 'Swing Time.' See, e.g., p. 4.
1999 Ficor catalog, listing the varieties 'Velvet Time' and 'Swing Time.' See, e.g., p. 4.
2000 Ficor catalog, listing the variety 'Swing Time.' See, e.g., p. 4.
2001 Ficor catalog, listing the variety 'Swing Time.' See, e.g., p. 4.
2002 Ficor catalog, listing the variety 'Swing Time.' See, e.g., p. 4.

* cited by examiner

*Primary Examiner*—Anne Marie Grunberg
*Assistant Examiner*—June Hwu
(74) *Attorney, Agent, or Firm*—Howrey Simon Arnold & White, LLP

(57) ABSTRACT

A new variety of Chrysanthemum plant named 'Safari Time Golden,' having golden yellow quill single flowers with spoon tips. The variety has a medium tall vigor with a free branching habit and good foliage presentation.

1 Drawing Sheet

Latin name of the genus and species: Botanical classification: *Chrysanthemum morifolium.*

Variety denomination: The new Chrysanthemum variety denomination is 'Safari Time Golden'.

BACKGROUND OF THE INVENTION

The present invention comprises a new and distinct cultivar of Chrysanthemum botanically known as *Chrysanthemum morifolium,* and referred to by the cultivar name 'Safari Time Golden.' 'Safari Time Golden,' identified as 21912-0, originated from a cross made in a controlled breeding program in Chichester, West Sussex, United Kingdom. The female parent of the new variety is the unpatented variety known as 'Velvet Time.' The male parent of the new variety is the unpatented variety known as 'Swing Time.' The new variety 'Safari Time Golden' has been asexually reproduced by vegetative cuttings in Chichester, West Sussex, United Kingdom and the distinguishing characteristics are retained through successive generations of asexual reproduction.

BRIEF SUMMARY OF THE INVENTION

'Safari Time Golden' is a pot type of Chrysanthemum plant variety having golden yellow single quill flowers with spoon tips.

Comparison with Female Parent

Plants of the new Chrysanthemum variety 'Safari Time Golden' are dissimilar to the female parent 'Velvet Time' in plant habitat and growth rate. In side-by-side comparisons in Chichester, West Sussex, United Kingdom, under commercial practice, plants of the new Chrysanthemum variety 'Safari Time Golden' differed from plants of the female parent 'Velvet Time' in the following characteristics.

1. The new variety 'Safari Time Golden' produces golden yellow quill single flowers whereas the female parent 'Velvet Time' produces purple single flowers.
2. Plants of the new variety 'Safari Time Golden' have larger and taller inflorescence than plants of the female parent 'Velvet Time.'

Comparison with Male Parent

Plants of the new Chrysanthemum variety 'Safari Time Golden' are dissimilar to the male parent 'Swing Time' in plant habitat and growth rate. In side-by-side comparisons in Chichester, West Sussex, United Kingdom, under commercial practice, plants of the new Chrysanthemum variety 'Safari Time Golden' differed from plants of the male parent 'Swing Time' in the following characteristics.

1. The new variety 'Safari Time Golden' produces golden yellow quill single flowers whereas the parent 'Swing Time' produces orange single flowers.
2. Plants of the new variety 'Safari Time Golden' have larger and taller inflorescence than plants of the parent 'Swing Time.'

Comparison with Other Varieties

Plants of the new Chrysanthemum variety 'Safari Time Golden' are dissimilar to 'Trendy Time,' (U.S. Plant Pat. No. 11,447) in plant habitat and growth rate. In side-by-side comparisons in Chichester, West Sussex, United Kingdom, under commercial practice, plants of the new Chrysanthemum variety 'Safari Time Golden' differed from plants of 'Trendy Time' in the following characteristics.

1. The new variety 'Safari Time Golden' produces golden yellow flowers whereas 'Trendy Time' produces saffron-yellow flowers.
2. Plants of the new variety 'Safari Time Golden' have larger and taller inflorescence than plants of 'Trendy Time.'
3. The new variety 'Safari Time Golden' has longer but fewer quills than the variety 'Trendy Time.'

BRIEF DESCRIPTION OF ILLUSTRATION

Typical specimens of the plant and flowers for the new Chrysanthemum variety 'Safari Time Golden' are shown in the accompanying digital photograph. The colors shown are as true as possible within the usual limits of this kind of illustration.

FIG. 1 is a whole plant view of the new variety 'Safari Time Golden' grown in a pot. The plant shown in the illustration is 60 days from the commencement of Short Days.

DETAILED BOTANICAL DESCRIPTION

The following description of the new Chrysanthemum variety 'Safari Time Golden' is of plants grown in a greenhouse in Chichester, West Sussex, United Kingdom in the month of May. The cultivar has not been observed under all possible environmental conditions. The phenotype may vary significantly with variations in the environment such as temperature, length of day and light intensity, without any variance in genotype. The commercial classification of the new variety is a pot Chrysanthemum.

Plants of the new variety have been grown successfully under temperature conditions averaging about 19° C. at night and about 17° C. to 24° C. during the day under light conditions of about 5000 to 6000 foot candles. The plants respond well to the use of growth retardant, such as B9 treatment at about 2 g per liter. To produce a commercial product the plants may be pinched once with the center bud removed. The typical container size for commercial growth is 1 liter. It has been observed that the shelf life of the new variety is about 25 days with a response time of about 7.5 weeks. The new variety is suitable for growth in a temperature range of 15° C. to 25° C.

The new variety may be produced as a spray. The following description is with respect to a plant produced as pot Chrysanthemum. In the description of this new Chrysanthemum variety, color values have been taken from The Royal Horticultural Society Colour Chart (R.H.S.C.C.).

Plant

Plant type: Pot
Habit: Upright
Height: 22 cm
Width: 34 cm.
Branching characteristics: Upright and free branching
Length of lateral branches: 16 cm
Number of breaks from pinch: 5
Stem color: 138B
Response time: 52 days
Vigor: Medium tall
Shelf life: 25 days
Disease/pest (susceptibility/resistance observed): None observed.
Growth retardant type and treatment: 3 applications of 2.5 gm/liter B9 @ 2, 21 and 28 days after sticking unrooted cuttings.
The plants were grown for 2 weeks in Long Day conditions (20 hours of light) and then transferred to Short Day conditions (13 hours of dark).
Propagation:
*Type.*—Vegetative propagation via stem cuttings.
*Time to rooting.*—14 days with soil temperatures of 18° C.
*Rooting habit.*—After 7 days the first roots emerge and form root primordia. In 14 Long Days a complete root system is developed.

Foliage

Number of leaves per lateral branch: 10
Compound or single: Single
Arrangement of leaves: Alternate
*Shape of leaf.*—Typically 5 lobed.
*Size of leaf.*—Width (cm): 6.5. Length (cm): 4.5.
*Leaf apex.*—Acute.
*Base.*—Obtuse.
*Attachment.*—Petioled.
*Aspect.*—Slightly undulating.
*Margin.*—Lobed.
*Surface characteristics.*—Top: slightly pubescent. Bottom: pubescent.
Petiole:
*Color.*—147A.
*Length.*—3 cm.
*Diameter.*—0.2 cm.
Venation: Net prominent mid vein at underside
*Color.*—Upper side: near 147B. Under side: near 137A.
Color: Mature Leaf, upper side: near 147A; under side: near 137A Young leaf, upper side: near 137B; under side: near 147A

Flower

Flower appearance: Matte
Flower type: Single quill
Flower form: Slightly cupped
Flower shape: Round
Flowering habit: Domed capitulum
Number of blossoms per branch: 5
Inflorescence form: Cyme
Depth of fully expanded blossoms: 2.5 cm
Diameter of fully expanded blossoms: 7.5 cm
Phyllaries:
*Number.*—23.
*Color.*—Near 138B.
*Length.*—1 cm.
*Width.*—0.2 cm.
*Texture/appearance.*—Slightly pubescent.
Peduncle: Peduncle length is shortest at the terminal flower and progressively longer moving down the stem.
*Length.*—12 cm (average).
*Color.*—Near 138A.
*Surface.*—Slightly pubescent.
*Habit.*—Slightly undulating.
*Strength.*—Medium.
Pedicel:
*Length.*—Terminal: 4 cm; lateral: 5 cm.
*Color.*—Near 138A.
*Surface.*—Slightly pubescent.

*Habit.*—Slightly undulating.
*Strength.*—Medium.
Ray florets:
*Form/shape.*—Straight quill with spoon tips.
*Texture/appearance.*—Matte.
*Number per flower.*—25.
*Length.*—4.5 cm; Width: 0.3 cm.
*Apex.*—Rounded.
*Base.*—Tapered.
*Margin.*—Entire.
Disc florets:
*Form/shape.*—Cylindric.
*Texture/appearance.*—Shiny.
*Number per flower.*—150.
*Length.*—0.4 cm; Width: 0.1 cm.
*Diameter of disc.*—1.4 cm.
Fragrance: none
Flower bud (at onset of color):
*Length.*—1 cm.
*Diameter.*—0.8 cm.
*Form/shape.*—Spherical.
General flower color:
1. *Ray florets, upper side.*—9B. Immature: near 9B. Mature: near 9B. Older/Fading: near 12B.
2. *Ray florets, under side.*—12B. Immature: near 12B. Mature: near 12B. Older/Fading: near 12C.
3. *Disc florets.*—Immature: near 151C. Mature: near 151C. Older/Fading: near 5A
4. *Bud.*—5B. .

Flower progression with age: flower form does not change but there is a slight color fading with age.
Lastingness of blooms is about 25 days.

Reproductive Organs

Gynoecium present on Ray and Disc florets:
Ray florets per individual flower:
*Pistil number.*—25.
*Stigma color.*—Near 5A.
*Stigma shape.*—Forked.
*Style color.*—Near 154C.
*Style length.*—0.4 cm.
Disc florets per individual flower:
*Pistil number.*—150.
*Stigma color.*—Near 5A.
*Stigma shape.*—Forked.
*Style color.*—Near 154C.
*Style length.*—0.4 cm.
Androecium not observed.
Fruit and Seeds: None observed.

What is claimed is:

1. A new and distinct variety of Chrysanthemum plant, substantially as described and illustrated herein.

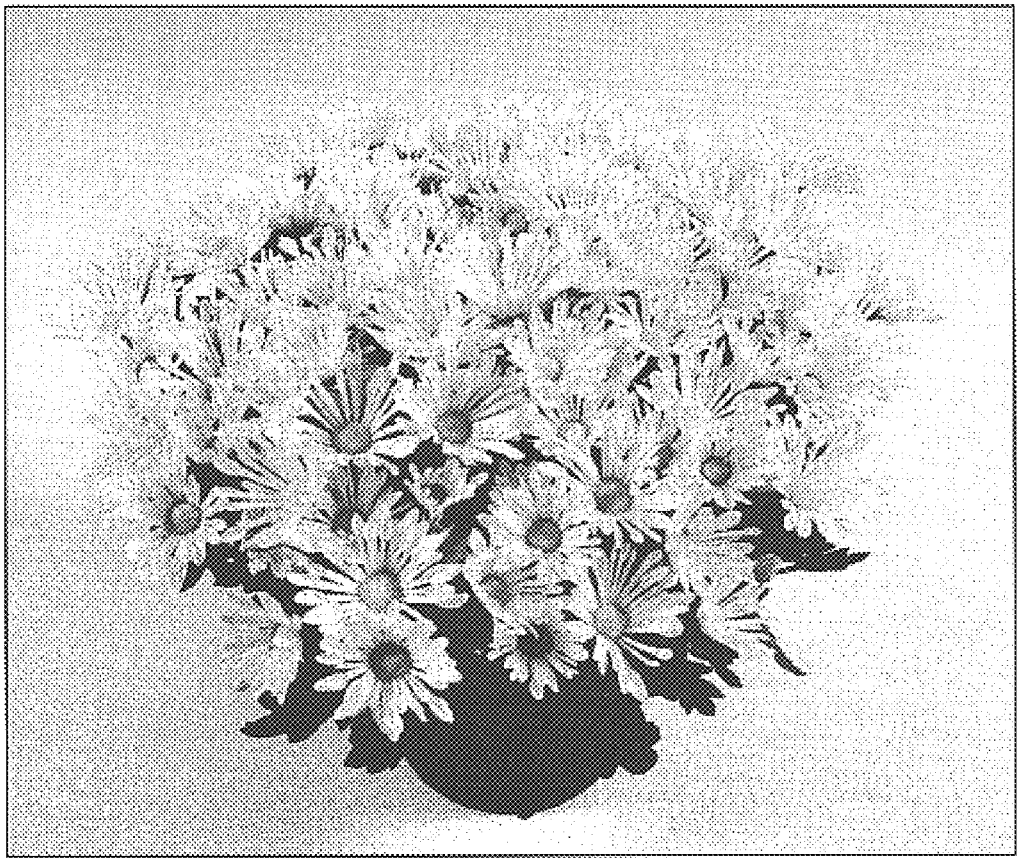

* * * * *